United States Patent [19]

Bogdon

[11] Patent Number: 4,493,642
[45] Date of Patent: Jan. 15, 1985

[54] ORTHODONTIC DEVICE AND ASSOCIATED ORTHODONTIC METHOD

[76] Inventor: Glendon J. Bogdon, 3044 S. 92nd St., Milwaukee, Wis. 53227

[21] Appl. No.: 453,460

[22] Filed: Dec. 27, 1982

[51] Int. Cl.³ .................................................. A61C 7/00
[52] U.S. Cl. .................................................. 433/5
[58] Field of Search .................................................. 435/5

[56] References Cited

U.S. PATENT DOCUMENTS 3,137,941  6/1964  Andrews .................. 433/5
4,378,210  3/1983  Uztzbe .................... 433/5

Primary Examiner—Robert Peshock

[57] ABSTRACT

An orthodontic device comprises a face bow member which includes generally diverging outer arms adapted for connection to an orthodontic headpiece and inner arms extending between the outer arms and adapted to project into the mouth of the user. A stem member is rotationally connected with each of the inner arms and is biased toward a given rotational position. An annular collar adapted for engagement with a tooth is removably connected on each of the stem members so that rotation of each stem member is transmitted into arcuate movement of the associated collar. When the collars are engaged on the teeth, the stem members are each located out of their normally biased position, so that the biasing force serves to arcuately move the collar. In use, the device applies a linear force to the body of the tooth to move the tooth toward the back of the mouth and another linear force to the body of a tooth to tip the crown of the tooth relative to the root while simultaneously applying a rotational force to the body of the tooth by virtue of the arcuate movement of the collars in response to the biasing force to also tip the root of the tooth in the same direction as the crown.

31 Claims, 8 Drawing Figures

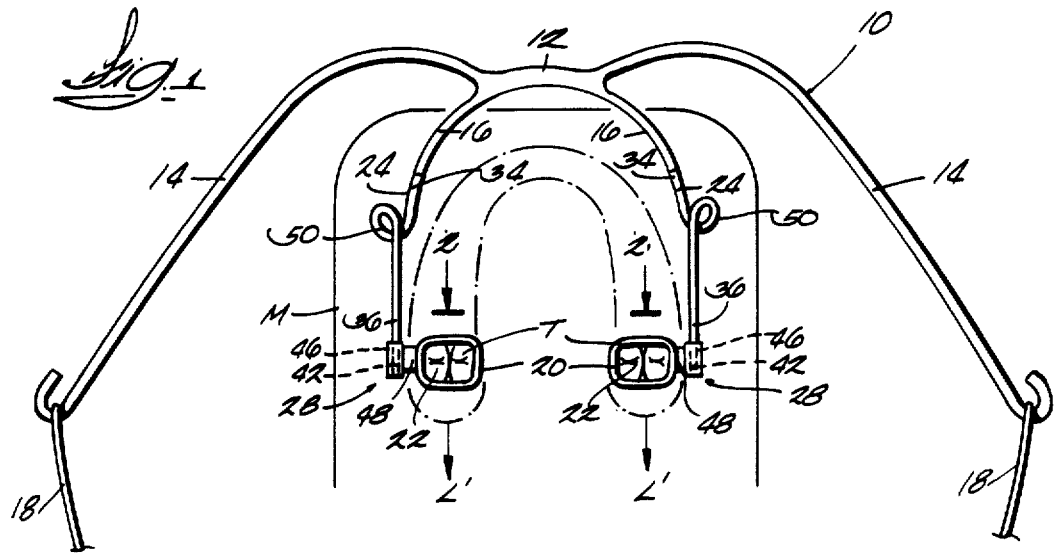
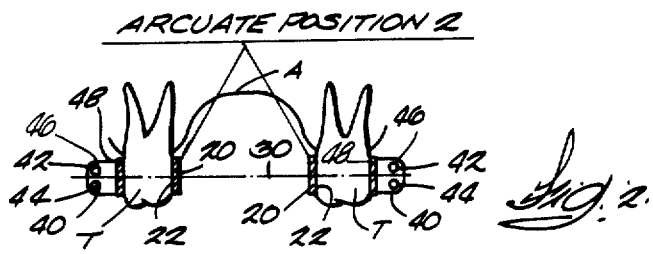
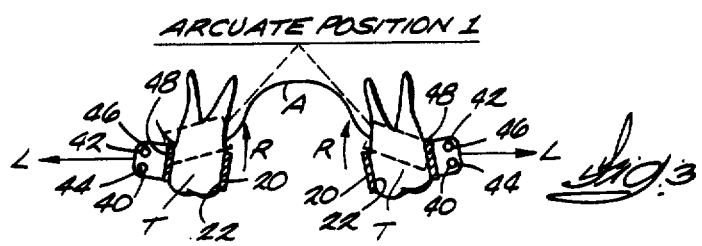
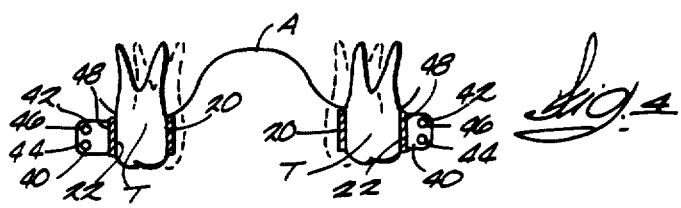
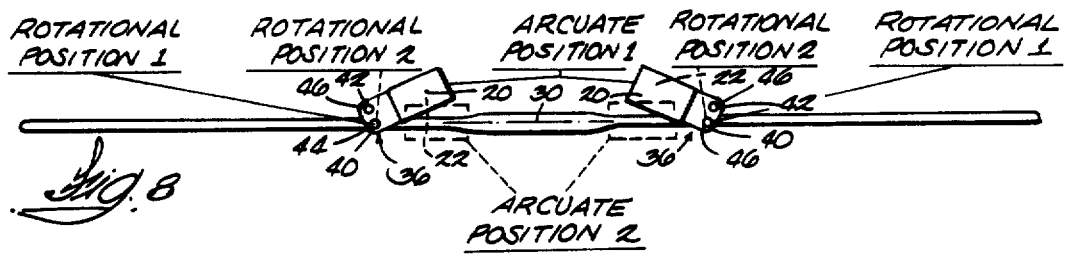

U.S. Patent  Jan. 15, 1985  Sheet 2 of 2  4,493,642
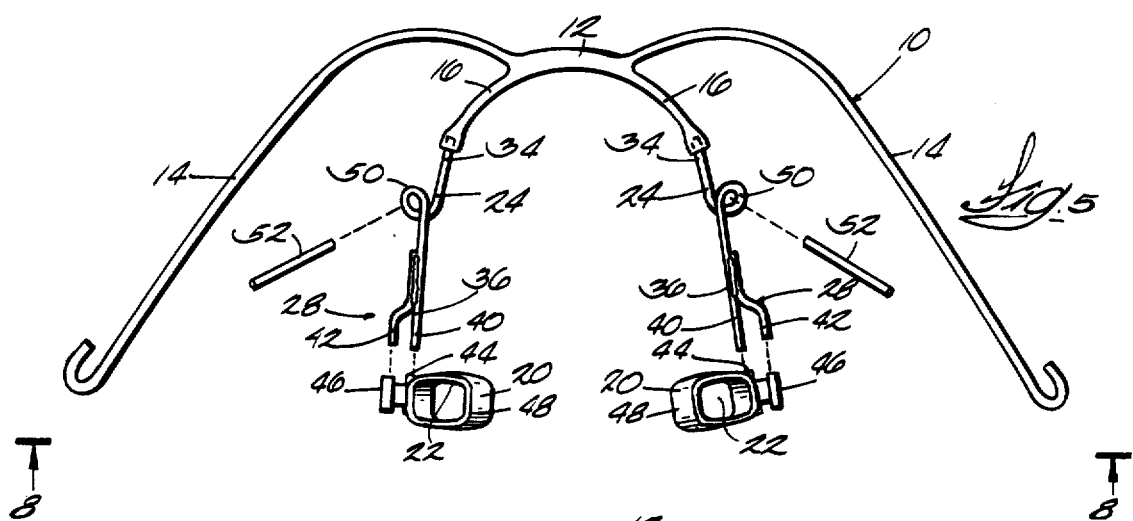
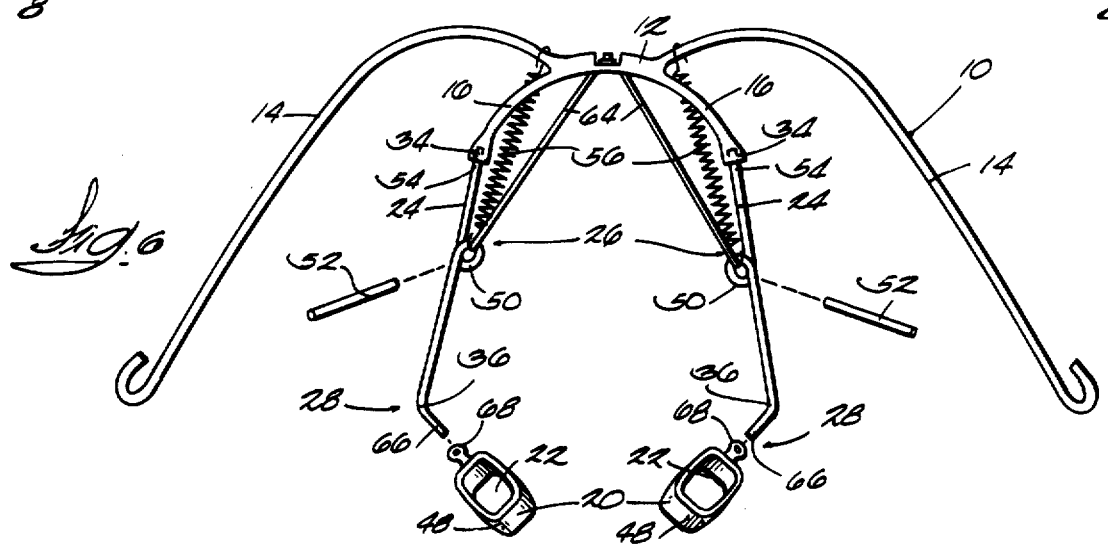
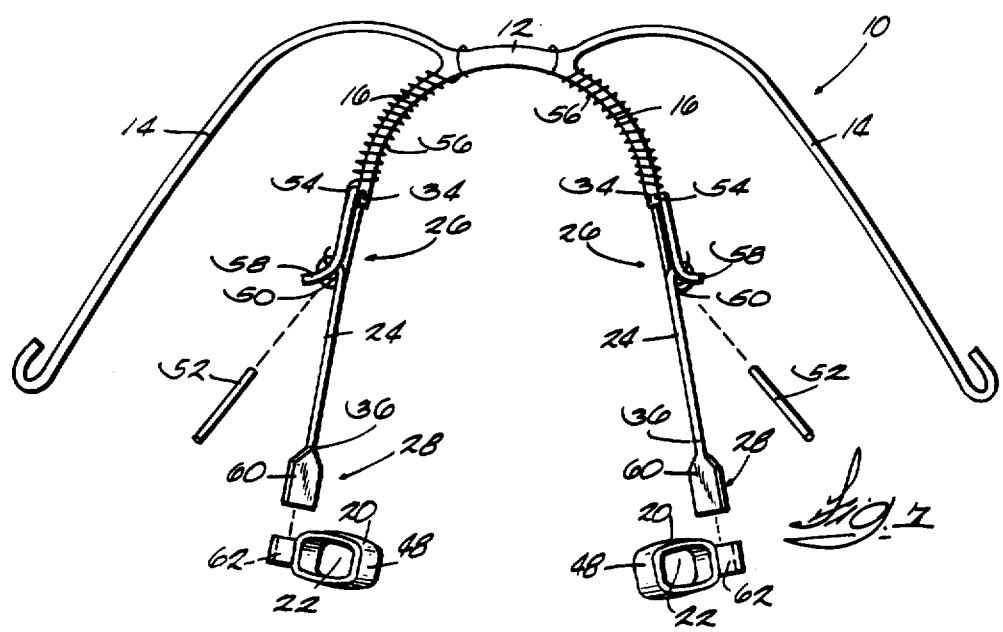

ORTHODONTIC DEVICE AND ASSOCIATED ORTHODONTIC METHOD

FIELD OF THE INVENTION

The invention generally relates to orthodontic devices and methods. More particularly, the invention relates to orthodontic devices and methods which apply traction to teeth to position the teeth on the maxillary or mandibular arches.

DESCRIPTION OF THE PRIOR ART

Orthodontic devices which utilize a face bow arrangement to apply traction to teeth are known and disclosed in the following U.S. patents:
Case—U.S. Pat. No. 862,881—Aug. 13, 1907
Walker—U.S. Pat. No. 1,217,374—Feb. 27, 1917
Asher—U.S. Pat. No. 3,121,953—Feb. 25, 1964
Andrews—U.S. Pat. No. 3,137,941—June 23, 1964
Stifter—U.S. Pat. No. 3,514,860—June 2, 1970
DeWoskin—U.S. Pat. No. 4,121,341—Oct. 24, 1978

All of the above face bow arrangements can be used to alter the position of teeth in the mouth by tipping the crowns of the teeth relative to their roots.

It is also desirable during the course of such orthodontic procedures to tip or "torque" the roots of the teeth in the direction of crown movement. This serves to bring the teeth into general upright vertical alignment in the mouth.

In conventional practice, "torquing" is typically undertaken after the crown has been tipped, entailing the use of additional orthodontic devices and steps. For example, an arch wire arrangement having generally rectilinear (instead of cylindrical) cross sections can be used for this purpose.

"Torquing" can also be accomplished by the use of a wire extending across the roof of the mouth between two oppositely spaced molars. In this procedure, the wire creates a force to tip the roots of the molars toward the cheek side of the mouth (facially).

SUMMARY OF THE INVENTION

It is one of the principal objects of this invention to provide an orthodontic device which, in addition to applying a linear force to the body of a tooth to tip the crown of the tooth, simultaneously applies a rotational force to the body of the tooth to torque or tip the root of the tooth in the same direction as the crown.

It is another principal object of this invention to provide an orthodontic device as just generally described which is applicable for use in a variety of corrective orthodontic procedures affecting tooth alignment in either the maxillary or mandibular arches.

To achieve these and other objects, the invention provides an orthodontic device which comprises a face bow member including generally diverging outer arms adapted for connection to an orthodontic headpiece and inner arms which extend between the outer arms and which are adapted to project into the mouth of the user. A first member is associated with each of the inner arms, and first means connects each of the first members to its associated inner arm for rotation relative thereto. A second member is associated with each of the first members and is adapted for engagement with a tooth. Second means removably connects each of the second members to the associated first member such that rotation of each of the first members is translated into arcuate movement of the associated second member. This arcuate movement applies a rotational force to the body of the tooth engaged by the second member and serves to tip or "torque" the root of the tooth in the direction of arcuate movement.

In one embodiment, each first member rotates relative to its associated inner arm between a first position and a range of positions rotationally spaced from the first position. In this embodiment, the first means includes means biasing each of the first members toward its first position, and the rotational force applied to the body of the tooth by arcuate movement of each second member is generated by the return of the first member toward its first position in response to the biasing force.

In one embodiment, the range of rotational positions includes a second position, and the second member includes an annular collar having a bore adapted for slip-fit engagement about the tooth. In this embodiment, the inner bow arms extend in a common plane, and it is in this common plane that the diameter of the collar bore extends when properly engaged with a tooth. With this in mind, the second means includes means for positioning the diameter of the annular collar bore in the common plane only when the associated first member is in its second rotational position.

DESCRIPTION OF THE DRAWINGS

FIG. 1 is a partially diagrammatic view of the inside of a patient's mouth looking toward the roof of the mouth and showing an orthodontic device which embodies various of the features of the invention in position on the maxillary arch of the patient;

FIG. 2 is a view taken generally along line 2—2 in FIG. 1, showing the tooth engaging collars associated with the orthodontic device as they are positioned at the outset of orthodontic procedures;

FIG. 3 is a view, similar to FIG. 2, showing the simultaneous linear and rotational forces being applied to the teeth by the orthodontic device during the course of orthodontic procedures;

FIG. 4 is a view, similar to FIGS. 2 and 3, showing the position of the teeth after orthodontic procedures using the orthodontic device are completed;

FIG. 5 is a plan and partially exploded view of the orthodontic device shown in FIG. 1;

FIG. 6 is a plan and partially exploded view with parts broken away and in section, of an alternate embodiment of an orthodontic device which embodies various of the features of the invention;

FIG. 7 is a plan and partially exploded view, with parts broken away and in section, of yet another alternate embodiment of an orthodontic device which embodies various of the features of the invention; and FIG. 8 is an end view of the orthodontic device taken generally along line 8—8 in FIG. 5 and showing the arcuate movement of the tooth engaging collars associated with the device.

Before explaining the embodiments of the invention in detail, it is to be understood that the invention is not limited in its application to the details of the construction and the arrangement of components set forth in the following description or illustrated in the drawings. The invention is capable of other embodiments and of being practiced and carried out in various ways. Also, it is to be understood that the phraseology and terminology being employed herein is for the purpose of description and should not be regarded as limiting.

GENERAL DESCRIPTION

Shown in FIG. 1 is an orthodontic device 10 which can be used to properly align teeth in a patient's mouth. The device 10 includes a generally resilient face bow member 12 which has diverging pairs of outer and inner arms, respectively, 14 and 16.

As shown in FIG. 1, the outer bow arms 14 are worn outside the patient's mouth (indicated by the letter M in FIG. 1) and are typically attached to a suitable orthodontic headstrap 18 worn by the patient. The inner bow arms 16 are worn inside the patient's mouth M and are suitably connected to the patient's teeth (indicated by the letter T in FIGS. 1 through 4).

More particularly (and referring now to FIG. 2 as well as FIG. 1), the device 10 includes a pair of members which, in the illustrated embodiment, take the form of annular collars or bands 20. Each of the collars includes a bore 22 adapted for slip-fit engagement about the body of the tooth T, and each collar 20 is operatively connected to an inner bow arm 16.

Typically, and as diagrammtically shown in FIG. 1, the collars 20 are fitted to the six-year molars located on the maxillary, or upper, arch of the patient (the maxillary arch is identified by the letter A in FIGS. 1 through 4). However, it should be realized that other points of attachment can be utilized, depending upon the particular orthodontic procedures required. Also depending upon the orthodontic needs of the patient, other teeth may be coupled to the engaged molars T by conventional temporary wire braces.

In conventional orthodontic practice, as is diagrammatically shown in FIG. 3, the face bow 12 applies a generally uniform linear force (indicated by arrows and the letter "L" in FIG. 3) to each of the collar engaged molars T in a direction outwardly toward the cheek side of the patient's mouth. The constant application of this outwardly directed linear force L will, in time, tip or pivot the crown of each of the molars T relative to its root toward the cheek side of the patient's mouth. Typically, in this procedure, each crown is displaced by approximately one or two millimeters, thereby widening the maxillary arch A of the patient for functional or cosmetic purposes. Arrows labeled L' in FIG. 1 show another direction of linear force applied by the orthodontic device during the course of orthodontic procedures.

During the course of this procedure, it is desirable to bring the "tipped" molars T (as shown in FIG. 3) into general up and down vertical alignment in the mouth (as shown in FIG. 4). With this in mind, the device 10 includes a member 24 which is rotationally connected to each of the inner bow arms 16 and to which a collar 20 is attached.

More particularly, and referring first to the embodiment illustrated in FIGS. 1 and 5, the member 24 takes the form of a generally cylindrical stem having opposite ends 34 and 36. The stem member 24 is made of a naturally resilient metallic or plastic material and is capable of being rotationally deformed or twisted out of its normal position by the application of an external force and then resiliently spring back to its normal position when the external force is removed.

In this embodiment, stem end 34 of each stem member 24 is secured, such as by welding or gluing, to the associated inner arm 16. As is shown in FIG. 8, each outwardly extending stem end 36 can thus be rotationally displaced relative to its secured end 34 by the application of an external force to resiliently twist the stem member 24 from a normal first, or untwisted, position (shown as Rotational Position 1 in solid lines in FIG. 8) through a range of positions rotationally spaced from its first position and including a second position (shown as Rotational Position 2 in phantom lines in FIG. 8). Upon the removal of the external "twisting" force, the natural resiliency of the stem member 24 serves to return the member 24 back toward Rotational Position 1. This naturally resilient movement is generally shown by arrows in FIG. 8.

The device 10 also includes means 24 which removably connects a molar engaging collar 20 to each member 24 such that the rotation of the associated member 24 is transmitted into the arcuate movement of the collar 20.

More particularly, in the embodiment shown in FIGS. 1 and 5, the means 28 includes a first prong 40 which extends axially from each of the outwardly extending stem ends 36, and a second prong 42 which extends axially of and generally co-extensively with the first prong 40. The means 28 further includes corresponding first and second channels 44 and 46 formed on the outer wall 48 of each of the associated collars 20. The first and second channels 44 and 46 extend in a direction which is transverse the axial bore 22 of the collars 20 and slidingly receive the first and second prongs 40 and 42, as can be seen in FIG. 1.

By virtue of this arrangement, each collar 20 extends toward the tongue side of the mouth at a right angle to the associated stem member 24. Rotation of each stem member 24 from Rotational Position 1 to Rotational Position 2 thus correspondingly moves the associated collar 20 in an arcuate path (shown by arrows in FIG. 8) from Arcuate Position 1 when the stem member 24 is in Rotational Position 1 (both of which positions are shown in solid lines in FIG. 8) to Arcuate Position 2 when the stem member 24 is in Rotational Position 2 (both of which positions are shown in Rotational Position 2), and vice versa.

As can also be seen in FIG. 8, the inner bow arms 16 and associated stem members 24 extend in a common plane 30. When the face bow 12 is being worn by the patient (see FIG. 2), this common plane 30 is generally parallel to the horizontal plane of the maxillary arch. As can also be seen in FIG. 2, the diameter of each collar bore 22 must also generally be located in this common plane 30 when the collar 20 is initially fitted on the associated molar T prior to the commencement of orthodontic procedures. As is shown in phantom lines in FIG. 8, the arrangement illustrated in FIGS. 1 and 5 positions the diameter of the collar bore 22 in this common plane 30 only when the respective collar 20 is in Arcuate Position 2, and each collar 20, in turn, is positioned in Arcuate Position 2 only after its associated stem member 24 has been resiliently twisted by an external force into Rotational Position 2. Of course, upon removal of this external force, each collar 20 will tend to move in response to the resilient return of the stem member 24 toward Rotational Position 1 arcuately out of the common plane 30 and back toward Arcuate Position 1 (as shown by arrows in FIG. 8).

Referring now to FIG. 3, this constant, normal tendency of each collar 20 to arcuately return from Arcuate Position 2 toward Arcuate Position 1 (shown in phantom lines in FIG. 3) generates a rotational force (indicated by arrows and the letter R in FIG. 3) which serves to tip the root of the tooth engaged by each collar 20 in the direction of arcuate movement. In the illustrated embodiment, the arcuate movement of collars 20 toward Arcuate Position 1 moves or torques the roots of each molar T toward the cheek-side of the patient's mouth. It should, of course, be appreciated that the direction of arcuate movement of each collar 20 could be reversed according to the objectives of the desired orthodontic procedures.

The rotational force generated by the device 10 is applied to the teeth simultaneously with the application, also by device 10, of the linear force L. As a result, and as can be seen in FIG. 4, the simultaneous application of linear force L and rotational force R by the device 10 ultimately locates each molar T (as shown in solid lines in FIG. 4) in a position which is not only outwardly displaced from its original position (as symbolized by the phantom position of tooth T in FIG. 4), but also in proper vertical, upright alignment in the mouth.

To facilitate the application of an external force to twist each stem member 24 from its normal or "untwisted" first position to its second position (i.e., from Rotational Position 1 to Rotational Position 2 in FIG. 8), thereby moving the associated collar 20 from Arcuate Position 1 to Arcuate Position 2 to provide a proper initial slip fit on the molars T prior to the undertaking of orthodontic procedures, a loop 50 is formed in each of the stems 24 intermediate its opposite ends 34 and 36, and one or more lever members 52 are provided which are operatively engageable in each of the loops 50. The members 52 define lever arms to facilitate the desired twisting of each of the stems 24.

Alternate embodiments of the device 10 are shown in FIGS. 6 and 7, and structural elements which are common to the embodiment shown in FIGS. 1, 5 and 8 are given common reference numerals. In both alternate embodiments, and like the first described embodiment, the member 24 takes the form of a stem having opposite ends 34 and 36. However, unlike the first embodiment, the stem 24 in both alternate embodiments is preferably not naturally resilient.

Instead, in these alternate embodiments, means is provided defining a sleeve 54 on the end of each inner bow arm 16. Each sleeve 54 rotationally receives end 34 of the associated stem member 24. Each stem member 24 is thus rotatable in the sleeve 54 relative to the associated inner arm 16 in the same manner as the stem member 24 in the first described embodiment is resiliently twistable relative to the associated inner arm 16.

In each alternate embodiment, means in the form of a spring 56 biases each of the stems 24 toward a given rotational position, which corresponds to Rotational Position 1 in FIG. 8.

As in the first described embodiment, a loop 50 is formed in each of the stems 24 in the FIGS. 6 and 7 embodiments, and the lever member 52 can be used to facilitate the rotation of each stem 24 away from its normally biased rotational position (i.e. Rotational Position 1).

In the FIG. 6 embodiment, the spring 56 extends between the loop 50 and the body of the face bow 12 adjacent to the junction of the outer and inner bow arms 14 and 16. In the FIG. 7 embodiment, the spring 56 extends about the inner bow arm 16 between the loop 50 and the body of the face bow 12 adjacent to the junction of the outer and inner arms 14 and 16. In either construction, the biasing force of the springs 56 serves to return the stem members 24 toward Rotational Position 1.

Furthermore, in these alternate embodiments, and unlike the first described embodiments, stop means 26 is provided which prevents the rotation of each stem member 24 toward its normally biased rotational position to proceed beyond that normally biased position.

While various constructions are possible, in the embodiment shown in FIG. 6, the stop means 26 takes the form of an overcenter assembly including a rubber band 64 or the like associated with each stem member 24. Each rubber band 64 is suitably attached to the face bow member 12 and extends about each loop 50. Each rubber band 64 prevents the return of its associated stem member 24 in response to its biasing force to proceed beyond its normally biased rotational position. Each rubber band 64 also provides a force which assists in the return of each associated stem member 24 toward its normally biased rotational position.

In the alternate embodiment shown in FIG. 7, the stop means 26 takes the form of member 58 which is attached on each inner bow arm 16 and against which the loop 50 of the associated stem 24 abuts when the stem 24 is in its normally biased rotational position. Like the overcenter assembly 64 in FIG. 6, the member 50 prevents rotation of the stem 24 beyond its normally biased rotational position in response to the biasing force of the spring 56.

To transform rotation of the stem members 24 in the FIGS. 6 and 7 embodiments into the desired arcuate movement of the collars 20 (as shown in FIG. 8 and previously described in connection with the FIGS. 1 and 5 embodiment), the means 28 in the FIG. 6 embodiment includes a cylindrical finger 66 which extends at generally a right angle from the outwardly extending stem end 36. In this arrangement, the means 28 further includes a channel 68 on the associated collar outer wall 48 into which the cylindrical finger 66 fits. The channel 68 extends axially of the axial bore 22 so that the collars 20 are normally positioned outside of plane 30 when the stem members 24 are in their biased first position. This position of the collars 20 is shown in solid lines in FIG. 6 and corresponds to Arcuate Position 1 in FIG. 8.

Thus, the FIG. 6 embodiment, as in the first described embodiment, to affect proper initial engagement of each collar 20 on the tooth T, each collar 20 must be arcuately moved into the position corresponding to Arcuate Position 2 in FIG. 8, by rotating the associated stem member 24 out of its normally biased rotational position (Rotational Position 1) into Rotational Position 2. After initial attachment, subsequent arcuate movement of each collar 20 in response to the biasing force of the spring 56 proceeds as shown in FIGS. 3 and 8, thereby tipping the root toward the cheek side of the mouth.

The same arcuate movement of each collar 20 is also accomplished in the FIG. 7 embodiment. In this embodiment, the means 28 includes a generally flattened, rectilinear finger 60 which extends outwardly from each outwardly extending stem end 36. In this arrangement, the means 28 further includes a matching rectilinear slot 62 on each of the outer walls 48 of the collars 20, into which slot 62 the finger 60 fits. The rectilinear slot 62, like the heretofore described channels 44 and 46 of the first embodiment, extends transversely of the axial collar bore 22 to affect the desired arcuate positioning of the collars 20 in Arcuate Position 1 (i.e., out of common plane 30) when the stem members 24 are in their normally biased rotational position.

Thus, as in the embodiments shown in FIGS. 1 and 5 and in FIG. 6, the diameter of each bore 22 extends in the common plane 30 only when the associated stem member 24 is located out of its normally biased rotational position. Accordingly, in this embodiment as in the ones previously described, the return of each stem member 24 toward its normally biased rotational position in response to the biasing force serves to arcuately move the associated collar 20, as shown in FIGS. 3 and 8, to tip the root of the tooth toward the cheek side of the patient's mouth.

The particular extent of arcuate movement of the collars 20 after initial engagement with the teeth T, as occasioned by the biased return of the stem member 24 toward its first rotational position, can vary according to the distance of the root must be moved as well as with the length of time during which the orthodontic procedure will occur. Generally, when root movement of one to two millimeters is envisioned, arcuate movement of approximately 45° (as generally shown in FIG. 8) is sufficient. The particular magnitude of the biasing force utilized can also vary according to the amount of root movement desired and the duration of orthodontic procedure envisioned. Generally speaking, a large biasing force is not needed, and any biasing force which assures a constant, uniform return of the stem member 24 toward its first position before engagement of the collars 20 with the teeth T is sufficient.

It should be appreciated that the three embodiments illustrated and described are not mutally exclusive. Structural features of any one of the embodiments may be adapted for use in combination with the structural features of any other of the embodiments.

It should also be appreciated that the device 10 as heretofore described is applicable for use, not only to align teeth outwardly on the maxillary arch, but, if necessary, can be used to position the teeth inwardly on the maxillary arch as well. The device 10 can likewise be used to position teeth inwardly or outwardly on the mandibular arch, if desired.

Various of the features of the invention are set forth in the following claims.

I claim:

1. An orthodontic device comprising
   a face bow member including generally diverging outer arms adapted for connection to an orthodontic headpiece and inner arms extending between said outer arms and adapted to project into the mouth of the user.
   a first member associated with each of said inner arms,
   first means connecting each of said first members to said associated inner arm for imparting to each of said first members a generally horizontal force directed outwardly toward the cheek side of the user's mouth, and for rotation of each of said first members about an axis fixed relative to said associated inner arm,
   a second member associated with each of said first members, each of said second members being adapted for engagement with a tooth, and
   second means removably connecting each of said second members to said associated first member for imparting to each of said second members said generally horizontal force imparted to said associated first member, and for transmitting rotation of said first member into arcuate movement of said second member about said axis, whereby arcuate movement of each of said second members applies a rotational force to the tooth and serves to tip the root of the tooth engaged by said second member in the direction of said arcuate movement.

2. An orthodontic device according to claim 1 wherein said first means connects each of said first members to said associated inner arm for rotation relative thereto between a first position and a range of positions rotationally spaced from said first position and includes means biasing each of said first members toward said first position, whereby arcuate movement of each of said second members in response to the biased return of said associated first member toward said first position tips the root of the tooth engaged by each second member.

3. An orthodontic device according to claim 2 wherein said range of positions includes a second position rotationally spaced from said first position,
   wherein said second member includes an annular collar having a bore adapted for slip fit engagement about the tooth,
   wherein said inner arms extend in a common plane, and
   wherein said second means includes means for positioning the diameter of said annular collar bore generally in said common plane only when said associated first member is generally in said second rotational position, whereby the return of each of said first members from said second position toward said first position in response to the biasing force arcuately moves said associated collar to tip the root of the tooth engaged by said collar.

4. An orthodontic device according to claim 1
   wherein said first member includes a resilient stem member having opposite ends and being resiliently deformable out of a normal position to rotationally displace one of said opposite ends relative to the other one of said opposite ends in response to the application of an external force and subsequently resiliently return to said normal position in response to the removal of the external force,
   wherein said first means includes means for securing one of said stem member ends to said associated inner arm to permit resilient rotational displacement of said opposite end relative to said secured end, and thus relative to said associated inner arm, in response to the application of the external force to resilient deform said stem member out of said normal position and the resilient return of said stem member back to said normal position in response to the removal of the external force, and
   wherein said second means connects each of said second members adjacent to said opposite end of said associated stem member for arcuate movement in response to the rotational displacement of said opposite end and, when each of said second members is engaged on a tooth, locates said associated stem member generally out of said normal position, whereby the resilient return of said associated stem member toward said normal position arcuately moves said associated second member to tip the root of the tooth engaged by said second member.

5. An orthodontic device according to claim 4
   wherein said first means includes a loop formed in each of said stem members generally intermediate said opposite ends and means operatively engageable with said loop and defining a lever arm for facilitating the deforming of said stem member out of said normal position in response to the application of the external force.

6. An orthodontic device according to claim 1
wherein each of said inner arms includes an end portion,
wherein said first member include a stem member having opposite ends,
wherein said first means includes means defining a sleeve on each of said inner arm end portions for supporting one of said stem member ends for rotation between a first position and a range of positions rotationally spaced from said first position, said first means further including means for biasing said stem member toward said first rotational position, and
wherein said second means connects each of said second members adjacent to said other opposite end of said associated stem member for arcuate movement in response to rotation of said associated stem member and, when each of said second members is engaged on a tooth, locates said associated stem member in a position in said range of rotational positions, whereby arcuate movement of each of said second members in response to the biased return of said associated stem member toward said first position tips the root of the tooth engaged by each second member.

7. An orthodontic device according to claim 6 wherein said biasing means includes a spring.

8. An orthodontic device according to claim 6 wherein said biasing means includes stop means for preventing rotation of said stem member toward said first position in response to the biasing force to proceed beyond said first position.

9. An orthodontic device according to claim 4 or 6 wherein said second member includes an annular collar having an axial bore adapted for slip fit engagement about a tooth, and wherein said second means includes a first prong extending axially from said other opposite stem end, a second prong extending axially outwardly of and generally coextensively with said first prong and means forming spaced first and second channels on said associated collar for slidingly receiving said first and second prongs.

10. An orthodontic device according to claim 9
wherein said collar includes an outer peripheral wall, and
wherein said first and second channels are formed on said collar outer wall and extend transversely of said axial bore.

11. An orthodontic device according to claim 4 or 6 wherein said second member includes an annular collar having an axial bore adapted for slip fit engagement about a tooth, and wherein aid second means includes a generally planar finger extending axially from said other opposite end of said stem member and means forming a generally rectilinear channel on said associated collar for slidingly receiving said planar finger.

12. An orthodontic device according to claim 11
wherein said collar includes an outer peripheral wall, and
wherein said rectilinear channel is formed on said collar outer wall and extends transversely of said axial bore.

13. An orthodontic device according to claim 4 or 6 wherein said second member includes an annular collar having an axial bore adapted for slip fit engagement about a tooth, and wherein said second means includes a finger extending from said other opposite end of said stem member at generally a right angle, and means forming a channel on said associated collar for slidingly receiving said finger.

14. An orthodontic device according to claim 13
wherein said collar includes an outer peripheral wall, and
wherein said channel is formed on said collar outer wall and extends axially of said axial bore.

15. An orthodontic device comprising
a face bow member including generally diverging outer arms, and inner arms extending between said outer arms and adapted to project into the mouth of the user,
an orthodontic headpiece,
first means connecting said face bow member to said orthodontic headpiece and imparting to each of said inner arms a generally horizontal uniform linear force directed outwardly toward the cheek side of the user's mouth,
a first member associated with each of said inner arms, said first member having opposite first and second ends,
second means connecting each first end of said first members to said associated inner arm for imparting to each of said first members said generally horizontal uniform linear force imparted to said associated inner arm, and for rotation of each second end of said first members about an axis fixed relative to said associated inner arm,
a second member associated with each of said first members, each of said second members being adapted for engagement with the crown of a tooth, and
third means removably connecting each of said second members to said second end of said associated first member for imparting to each of said second members said generally horizontal uniform linear force imparted to said associated first member, thereby imparting said force to the crown of the tooth and moving the crown of the tooth horizontally in the direction of said force, and for transmitting rotation of said second end of said associated first member into arcuate movement of said second member about said axis, whereby arcuate movement of each of said second members applies a rotational force to the tooth and serves to tip the root of the tooth engaged by said second member horizontally in the direction of the movement of the crown of the tooth.

16. An orthodontic device comprising
a face bow member including generally diverging outer arms adapted for connection to an orthodontic headpiece, and inner arms extending between said outer arms and adapted to project into the mouth of the user,
a first member associated with each of said inner arms, said first member including a resilient stem member having opposite ends and being resiliently deformable out of a normal position to rotationally displace one of said opposite ends relative to the other one of said opposite ends in response to the application of an external force and subsequently resiliently return to said normal position in response to the removal of the external force,
first means connecting each of said first members to said associated inner arm for rotation of each of said first members about an axis fixed relative to said associated inner arm, said first means including means for securing one of said stem member ends to said associated inner arm to permit resilient rotational displacement of said opposite end relative to said secured end, and thus relative to said associated inner arm, in response to the application of the external force to resiliently deform said stem member out of said normal position, and the resilient return of said stem member back to said normal position in response to the removal of the external force, said first means also including a loop formed in each of said stem members generally intermediate said opposite ends, and means operatively engageable with said loop and defining a lever arm for facilitating the deforming of said stem member out of said normal position in response to the application of the external force, a second member associated with each of said first members, each of said second members being adapted for engagement with a tooth, and second means removably connecting each of said second members to said associated first member for transmitting rotation of said first member into arcuate movement of said second member about said axis, whereby arcuate movement of each of said second members applies a rotational force to the tooth and serves to tip the root of the tooth engaged by said second member in the direction of said arcuate movement, said second means connecting each of said second members adjacent to said opposite end of said associated stem member for arcuate movement in response to the rotational displacement of said opposite end and, when each of said second members is engaged on a tooth, locating said associated stem member generally out of said normal position, whereby the resilient return of said associated stem member toward said normal position arcuately moves said associated second member to tip the root of the tooth engaged by said second member.

17. An orthodontic device according to claim 16 wherein said second member includes an annular collar having an axial bore adapted for slip fit engagement about a tooth, and wherein said second means includes a first prong extending axially from said other opposite stem end, a second prong extending axially outwardly of and generally coextensively with said first prong, and means forming spaced first and second channels on said associated collar for slidingly receiving said first and second prongs.

18. An orthodontic device according to claim 17 wherein said collar includes an outer peripheral wall, and wherein said first and second channels are formed on said collar outer wall and extend transversely of said axial bore.

19. An orthodontic device according to claim 16 wherein said second member includes an annular collar having an axial bore adapted for slip fit engagement about a tooth, and wherein said second means includes a generally planar finger extending axially from said other opposite end of said stem member, and means forming a generally rectilinear channel on said associated collar for slidingly receiving said planar finger.

20. An orthodontic device according to claim 19 wherein said collar includes an outer peripheral wall, and wherein said rectilinear channel is formed on said collar outer wall and extends transversely of said axial bore.

21. An orthodontic device according to claim 16 wherein said second rember includes an annular collar having an axial bore adapted for slip fit engagement about a tooth, and wherein said second means includes a finger extending from said other opposite end of said stem member at a generally right angle, and means forming a channel on said associated collar for slidingly receiving said finger.

22. An orthodontic device according to claim 21 wherein said collar includes an outer peripheral wall, and wherein said channel is formed on said collar outer wall and extends axially of said axial bore.

23. An orthodontic device comprising a face bow member including generally diverging outer arms adapted for connection to an orthodontic headpiece, and inner arms extending between said outer arms and adapted to project into the mouth of the user, each of said inner arms including an end portion, a first member associated with each of said inner arms, said first member including a stem member having opposite ends, first means connecting each of said first members to said associated inner arm for rotation of each of said first members about an axis fixed relative to said associated inner arm, said first means including means defining a sleeve on each of said inner arm end portions for supporting one of said stem member ends for rotation between a first position and a range of positions rotationally spaced from said first position, said first means further including means for biasing said stem member toward said first rotational position, a second member associated with each of said first members, each of said second members being adapted for engagement with a tooth, and second means removably connecting each of said second members to said associated first member for transmitting rotation of said first member into arcuate movement of said second member about said axis, whereby arcuate movement of each of said second members applies a rotational force to the tooth and serves to tip the root of the tooth engaged by said second member in the direction of said arcuate movement, said second means connecting each of said second members adjacent to said other opposite end of said associated stem member for arcuate movement in response to rotation of said associated stem member and, when each of said second members is engaged on a tooth, locating said associated stem member in a position in said range of rotational positions, whereby arcuate movement of each of said second members in response to the biased return of said associated stem member toward said first position tips the root of the tooth engaged by each second member.

24. An orthodontic device according to claim 23 wherein said biasing means includes a spring.

25. An orthodontic device according to claim 23 wherein said biasing means includes stop means for preventing rotation of said stem member toward said first position in response to the force biasing said stem member to said first position.

26. An orthodontic device according to claim 23 wherein said second member includes an annular collar having an axial bore adapted for slip fit engagement about a tooth, and wherein said second means includes a first prong extending axially from said other opposite stem end, a second prong extending axially outwardly of and generally coextensively with said first prong, and means forming spaced first and second channels on said associated collar for slidingly receiving said first and second prongs.

27. An orthodontic device according to claim 26 wherein said collar includes an outer peripheral wall, and wherein said first and second channels are formed on said collar outer wall and extend transversely of said axial bore.

28. An orthodontic device according to claim 23 wherein said second member includes an annular collar having an axial bore adapted for slip fit engagement about a tooth, and wherein said second means includes a generally planar finger extending axially from said other opposite end of said stem member, and means forming a generally rectilinear channel on said associated collar for slidingly receiving said planar finger.

29. An orthodontic device according to claim 28 wherein said collar includes an outer peripheral wall, and wherein said rectilinear channel is formed on said collar outer wall and extends transversely of said axial bore.

30. An orthodontic device according to claim 23 wherein said second member includes an annular collar having an axial bore adapted for slip fit engagement about a tooth, and wherein said second means includes a finger extending from said other opposite end of said stem member at generally a right angle, and means forming a channel on said associated collar for slidingly receiving said finger.

31. An orthodontic device according to claim 30 wherein said collar includes an outer peripheral wall, and wherein said channel is formed on said collar outer wall and extends axially of said axial bore.

* * * * *